US012648238B2

(12) United States Patent
Li et al.

(10) Patent No.: US 12,648,238 B2
(45) Date of Patent: Jun. 2, 2026

(54) METHODS AND STRUCTURES TO IMPROVE LIGHT COLLECTION EFFICIENCY IN BIOSENSORS

(71) Applicant: MGI Tech Co., Ltd., Shenzhen (CN)

(72) Inventors: Shifeng Li, Fremont, CA (US); Cheng Frank Zhong, Menlo Park, CA (US)

(73) Assignee: MGI Tech Co., Ltd., Shenzhen (CN)

( * ) Notice: Subject to any disclaimer, the term of this patent is extended or adjusted under 35 U.S.C. 154(b) by 1384 days.

(21) Appl. No.: 17/296,935

(22) PCT Filed: Nov. 29, 2019

(86) PCT No.: PCT/CN2019/121837
§ 371 (c)(1),
(2) Date: May 25, 2021

(87) PCT Pub. No.: WO2020/108588
PCT Pub. Date: Jun. 4, 2020

(65) Prior Publication Data
US 2021/0399030 A1 Dec. 23, 2021

Related U.S. Application Data

(60) Provisional application No. 62/774,239, filed on Dec. 1, 2018.

(51) Int. Cl.
*H10F 39/12* (2025.01)
*C12Q 1/6825* (2018.01)
(Continued)

(52) U.S. Cl.
CPC ......... *H10F 39/199* (2025.01); *C12Q 1/6825* (2013.01); *G01N 21/6428* (2013.01);
(Continued)

(58) Field of Classification Search
CPC ...... H01F 39/199; H01F 77/12; H01F 77/306; C12Q 1/6825; G01N 21/6428; G01N 21/6454; G01N 21/76; G01N 2021/6439
See application file for complete search history.

(56) References Cited

U.S. PATENT DOCUMENTS 8,686,529 B2 4/2014 Bui et al.
2004/0023253 A1* 2/2004 Kunwar ............. G01N 33/5438
205/777.5
(Continued)

FOREIGN PATENT DOCUMENTS

CN 101907573 A 12/2010
CN 102183511 A 9/2011
(Continued)

OTHER PUBLICATIONS

European Application No. 24163302.3, Extended European Search Report mailed on Jun. 6, 2024, 9 pages.
(Continued)

*Primary Examiner* — Charles Capozzi
*Assistant Examiner* — Alex Ramirez
(74) *Attorney, Agent, or Firm* — Kilpatrick Townsend & Stockton LLP

(57) ABSTRACT

A photodiode (112, 200, 400, 500) includes a semiconductor substrate (210) having a first surface (211) and a second surface (212, 412, 512), and a light sensing junction (220) located adjacent to the first surface (211). The second surface (212, 412, 512) is located opposite the first surface (211), and the second surface (212, 412, 512) includes a concave surface covering a recessed region (415, 515) in the semiconductor substrate (210).

14 Claims, 6 Drawing Sheets

(51) Int. Cl.

| | | |
|---|---|---|
| *G01N 21/64* | (2006.01) | |
| *G01N 21/76* | (2006.01) | |
| *H10F 77/12* | (2025.01) | |
| *H10F 77/30* | (2025.01) | |

(52) U.S. Cl.

CPC ......... *G01N 21/6454* (2013.01); *G01N 21/76* (2013.01); *H10F 77/12* (2025.01); *H10F 77/306* (2025.01); *G01N 2021/6439* (2013.01)

(56) References Cited

U.S. PATENT DOCUMENTS

| | | | | |
|---|---|---|---|---|
| 2004/0234417 A1* | 11/2004 | Schienle | ............ | G01N 21/6454 422/82.08 |
| 2010/0204064 A1* | 8/2010 | Cho | ................... | G01N 21/6454 506/17 |
| 2011/0175188 A1 | 7/2011 | Bui et al. | | |
| 2014/0203340 A1* | 7/2014 | Kraft | ..................... | H10F 30/221 438/98 |
| 2016/0341656 A1* | 11/2016 | Liu | ...................... | G01N 21/648 |

FOREIGN PATENT DOCUMENTS

| | | | |
|---|---|---|---|
| CN | 103597600 | B | 2/2014 |
| CN | 107084964 | A | 8/2017 |
| CN | 108511476 | A | 9/2018 |
| EP | 2362418 | A2 | 8/2011 |
| TW | 201702575 | A | 1/2017 |
| TW | 201719877 | A | 6/2017 |
| TW | 201737478 | A | 10/2017 |
| TW | 201830004 | A | 8/2018 |
| WO | 2018085642 | A1 | 5/2018 |
| WO | 2018175341 | A1 | 9/2018 |

OTHER PUBLICATIONS

PCT/CN2019/121837 , "International Search Report and Written Opinion", Feb. 21, 2020, 9 pages.

European Application No. 19888911.5, Extended European Search Report mailed on Jul. 22, 2022, 10 pages.

* cited by examiner

METHODS AND STRUCTURES TO IMPROVE LIGHT COLLECTION EFFICIENCY IN BIOSENSORS

CROSS-REFERENCES TO RELATED APPLICATIONS

This application claims benefit and is a 371 application of PCT Application No. PCT/CN2019/121837, filed Nov. 29, 2019, which claims priority to U.S. Provisional Patent Application No. 62/774,239, filed Dec. 1, 2018, entitled "Methods And Structures To Improve The Light Collection Efficiency," which is commonly assigned and incorporated by reference in their entirety herein for all purposes.

FIELD

The present invention relates generally to methods and structures for photodiodes and biosensors for biological or chemical analysis.

BACKGROUND

CMOS image sensors find use in electronic imaging devices, including digital cameras, medical imaging equipment, radar devices, and the like. Using integrated circuits and a series of photodiodes, CMOS image sensors can capture light and convert it into electrical signals.

CMOS image sensors are typically implemented on integrated circuit chips. The chips may have an amplifier for each pixel. Although the inclusion of many amplifiers in a chip may result in less area for the capture of light, other components can be integrated onto the chip to direct more light into the photodiodes. For example, microlenses may be placed in front of the photodiodes to direct light into the photodiodes. To further increase the amount of light that hits the photodiodes, backside illumination (BSI) can be used. BSI effectively places the photodiodes closer to the light source, instead of under and between the integrated circuit wiring, reducing destructive interference. BSI CMOS sensors also have other advantages. For example, BSI CMOS sensors may have low operating voltage, low power consumption, high efficiency, and low noise.

BSI CMOS image sensors typically have two functional areas: a light sensing area and an electronic circuit area. The light sensing area includes the photodiodes arranged in an array, coupled to metal-oxide-semiconductor (MOS) transistors that detect the light intensity. The electronic circuit area provides connections between the MOS transistors and external connections, such as to other devices for processing the data from the MOS transistors.

In practice, a BSI CMOS image sensor may employ filters that divide incident light into bands of light of different wavelengths. The light is received by the photodiodes on a substrate and transformed into electrical signals of different intensity. For example, an incident beam may be divided into red, green, and blue light and received by respective photodiodes for each color. Each photodiode transforms the detected light intensity into electrical signals. This is accomplished by the photodiode accumulating a charge. For example, the higher the intensity of the light, the higher the charge accumulated in the photodiode. The accumulated charge can then be correlated to a color and brightness.

In addition to the uses described above, CMOS image sensors may also be used for biological or chemical analysis. For such analysis, a biological or chemical sample may be placed above a photodiode, and light emitted by the biological or chemical sample may be directed to the photodiode. The fluorescence or chemiluminescence of the sample can be detected by the photodiode, and a color and brightness can be determined. This color and brightness may be used to identify the biological or chemical sample.

SUMMARY

Embodiments of the invention address the drawbacks associated with previous approaches by providing photodiodes that can improve light collection efficiency in biosensors for biological or chemical analysis.

According to embodiments of the invention, BSI CMOS image sensors can be used to effectively analyze and measure fluorescence or chemiluminescence of a sample. This measured value can be used to help identify a sample. Embodiments of the invention also provide methods of manufacturing an improved biosensor for biological or chemical analysis. As used herein, the term "biosensor" may be used to refer to an apparatus for determining a light emitting substance within or attached to a biological molecule, particularly a nucleic acid macromolecule exemplified by DNA and branched or otherwise derivatized nucleic acids. As used herein, the term "nucleic acid macromolecule" may refer to, for example, DNB or single strand embodiments.

According to some embodiments of the invention, methods and structures are provided for increasing collection of light emitted by fluorescence or chemiluminescence of a sample. In some embodiments, a photodiode can include a semiconductor substrate having a first surface and a second surface and a light sensing junction located adjacent to the first surface. The second surface is located opposite the first surface, the second surface comprises a concave surface covering a recessed region in the semiconductor substrate.

In some embodiments of the above photodiode, the recessed region is sized and functionalized to contain a nucleic acid macromolecule.

In some embodiments, the semiconductor substrate comprises a silicon material.

In some embodiments, the light sensing junction comprises a P-N junction.

In some embodiments, the light sensing junction comprises a P+ region in an N type substrate.

In some embodiments, the light sensing junction comprises a N+ region in a P-type substrate.

In some embodiments, the photodiode also includes a metal oxide layer overlying the second surface of the semiconductor substrate, and an oxide layer overlying the metal oxide layer.

In some embodiments, the metal oxide layer comprises a sandwiched thin layers of tantalum oxide ($Ta_2O_5$) and hafnium oxide ($HfO_2$), the oxide layer comprises silicon oxide.

In some embodiments, the photodiode also includes one or more metal oxide layer overlying the second surface of the semiconductor substrate, and a silicon oxide layer overlying the metal oxide layer.

In some embodiments, the metal oxide layer comprises one or more of hafnium oxide ($HfO_2$) and tantalum oxide ($Ta_2O_5$).

In some embodiments, the metal oxide layer comprises one or more of anodized aluminum ($Al_2O_3$), tantalum oxide ($Ta_2O_5$), niobium oxide ($Nb_2O_5$), zirconium oxide ($ZrO_2$), and titanium oxide ($TiO_2$).

In some embodiments, the recessed region in the semiconductor substrate is formed using a dry etching process.

In some embodiments, the dry etching process comprises a chlorine-based etching process or a fluorine-based dry etching process.

In some embodiments, the recessed region in the semiconductor substrate is formed using a wet etching process.

In some embodiments, the wet etching process comprises a crystalline orientation dependent wet anisotropic etch.

In some embodiments, the wet etching process comprises an etching process using KOH.

According to some embodiments, a biosensor can have a backside illumination complementary metal-oxide-semiconductor (CMOS) image sensor that includes an electronic circuit layer, and a photo sensing layer over the electronic circuit layer. The photo sensing layer includes a plurality of photodiodes overlying the electronic circuit layer. Each of the photodiodes has a light sensing junction adjacent to the electronic circuit layer and a light receiving surface opposite to the electronic circuit layer. The light receiving surface includes a concave surface covering a recessed region in a backside of the photodiode, and the recessed region is sized and functionalized to contain a nucleic acid macromolecule.

In some embodiments of the above biosensor, each of the photodiodes includes a photodiode as described herein.

In some embodiments, the electronic circuit layer includes a dielectric layer and a metal wiring formed in the first dielectric layer, wherein the metal wiring is configured to couple the plurality of photodiodes to an external device.

In some embodiments, the biosensor also includes a passivation layer over the backside illumination CMOS image sensor.

In some embodiments of the above biosensor, each photodiode of the plurality of photodiodes is configured to detect light emitted from a fluorescent or chemiluminescent label on a nucleic acid macromolecule of the plurality of nucleic acid macromolecules.

In some embodiments, the light is emitted from fluorescent labeled oligonucleotide probes hybridized to nucleic acid amplicons immobilized on the spots.

In some embodiments, the light is emitted from fluorescent labeled primer extension product hybridized to nucleic acid amplicons immobilized on the spots.

In some embodiments, the nucleic acid amplicons are from genomic DNA fragments or a cDNA library.

In some embodiments, the amplicons are formed by rolling circle amplification or bridge polymerase chain reaction (PCR).

In some embodiments, the biosensor also includes an excitation light source.

Some embodiments provide a method that includes providing a backside illumination complementary metal-oxide-semiconductor (CMOS) image sensor. Providing the backside illumination CMOS image sensor includes providing an electronic circuit layer and providing a photo sensing layer over the electronic circuit layer. The photo sensing layer includes an electronic circuit layer and a photo sensing layer over the electronic circuit layer. The photo sensing layer includes a plurality of photodiodes overlying the electronic circuit layer. Each of the photodiodes has a light sensing junction adjacent to the electronic circuit layer and a light receiving surface is defined by a surface of the plurality of photodiodes opposite to the electronic circuit layer. The light receiving surface includes a concave surface covering a recessed region in a backside of the photodiodes. The recessed region is sized and functionalized to contain a nucleic acid macromolecule.

In some embodiments of the above method, each of the photodiodes includes a photodiode as described herein.

In some embodiments, the light emitted from the nucleic acid macromolecule contained in the spot is received by the light receiving surface of one photodiode.

In some embodiments, the light emitted from the nucleic acid macromolecule contained in the spot is received from the light receiving surface of more than one photodiode.

In some embodiments, providing the electronic circuit layer includes depositing a dielectric layer and forming a metal wiring in the dielectric layer. The metal wiring is configured to couple the plurality of photodiodes to an external device.

In some embodiments, the method also includes depositing a passivation layer over the backside illumination CMOS image sensor.

In some embodiments, the method also includes attaching a nucleic acid macromolecule of the plurality of nucleic acid macromolecules to a spot of the plurality of spots.

In some embodiments, the method also includes detecting light emitted from a fluorescent or chemiluminescent label on the nucleic acid macromolecule using a photodiode of the plurality of photodiodes.

In some embodiments, the light is emitted from fluorescent labeled oligonucleotide probes hybridized to nucleic acid amplicons immobilized on the spots.

In some embodiments, the light is emitted from fluorescent labeled primer extension product hybridized to nucleic acid amplicons immobilized on the spots.

In some embodiments, the nucleic acid amplicons are from genomic DNA fragments or a cDNA library.

In some embodiments, the amplicons are formed by rolling circle amplification or bridge polymerase chain reaction (PCR).

In some embodiments, the method also includes illuminating the nucleic acid macromolecule with an excitation light source.

According to some embodiments, a method of nucleic acid sequencing includes iteratively performing a process that includes the following steps:

labeling a nucleic acid macromolecule with a fluorescent label that identifies a nucleotide base at a particular position in the nucleic acid macromolecule;

detecting the fluorescent label associated with the nucleic acid macromolecule, wherein detecting the fluorescent label includes:

illuminating the nucleic acid macromolecule with excitation light, wherein the nucleic acid macromolecule absorbs the excitation light and transmits emitted light onto a photodiode of a backside illumination (BSI) complementary metal-oxide-semiconductor (CMOS) image sensor;

measuring at least one parameter of the emitted light received at the photodiode; and correlating the at least one parameter of the emitted light to the fluorescent label; and removing the fluorescent label from the nucleic acid macromolecule.

In some embodiments of the above method, each of the photodiodes includes a photodiode as described herein.

According to some embodiments, a method of nucleic acid sequencing comprising iteratively performing a process that includes the following steps:

labeling a nucleic acid macromolecule with a chemiluminescent label that identifies a nucleotide base at a particular position in the nucleic acid macromolecule;

modifying the environment of the nucleic acid macromolecule chemiluminescent such that the label emits light;

wherein the emitted light is transmitted onto a photodiode of a backside illumination (BSI) complementary metal-oxide-semiconductor (CMOS) image sensor;

measuring at least one parameter of the emitted light received at the photodiode; and correlating the at least one parameter of the emitted light to the chemiluminescent label; and removing the chemiluminescent label from the nucleic acid macromolecule.

In some embodiments of the above method, each of the photodiodes includes a photodiode as described herein.

According to some embodiments, a biosensor has a backside illumination complementary metal-oxide-semiconductor (CMOS) image sensor that includes an electronic circuit layer and a photo sensing layer over the electronic circuit layer. The photo sensing layer includes a plurality of photodiodes overlying the electronic circuit layer. Each of the photodiodes has a light sensing junction adjacent to the electronic circuit layer and a light receiving surface is defined by a surface of the plurality of photodiodes opposite to the electronic circuit layer. The light receiving surface includes a concave surface covering a recessed region in a backside of the photodiodes. A protective layer above the light receiving surface that is sized and functionalized to contain a plurality of nucleic acid macromolecules.

In some embodiments of the above method, each of the photodiodes includes a photodiode as described herein.

The foregoing, together with other features and embodiments, will become more apparent upon referring to the following specification, claims, and accompanying drawings.

DETAILED DESCRIPTION

Figure 1:
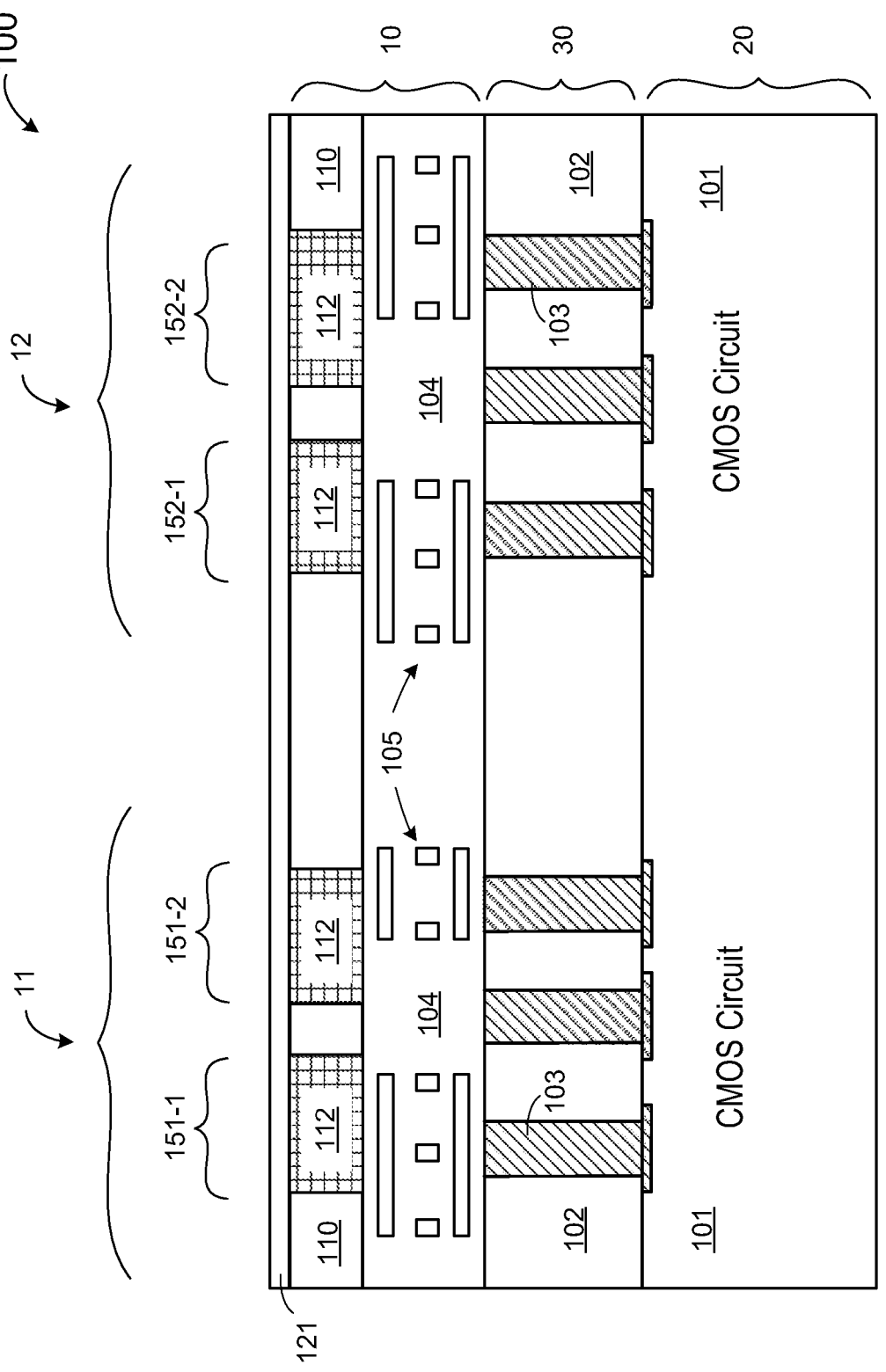
FIG. 1 is a cross-sectional view of a semiconductor wafer that includes a plurality of backside illumination (BSI) CMOS image sensors according to some embodiments of the invention.

FIG. 1 is a cross-sectional view of a semiconductor wafer that includes a plurality of backside illumination (BSI) CMOS image sensors according to some embodiments of the invention. In the manufacturing of semiconductor-based sequencing cells, a wafer can have thousands of dies, and each die represents a portion of the wafer that will be fabricated into a sequencing chip including an array of multiple cells, for example, hundreds of cells or more. For simplicity, FIG. 1 only shows regions 11 and 12 in semiconductor wafer 100, which are designed for two flow cells in two separate dies, and each region is shown to have only two cell areas, which are illustrated in FIG. 1. Region 11 includes cell areas 151-1 and 151-2, and region 12 includes cell areas 152-1 and 152 2.

As shown in FIG. 1, semiconductor wafer 100 includes CMOS image sensor layer 10, CMOS processing circuitry layer 20, and stacking layer 30. In a stacked technology, CMOS image sensor layer 10 and CMOS processing circuitry layer 20 can be fabricated separately and then joined together in a 3-D stacked device with a stacking interface layer 30.

CMOS image sensor layer 10 includes light sensing components, e.g., photodiodes 112, formed in a semiconductor layer 110. Semiconductor layer 110 may be made of any suitable material, such as, for example, silicon, III-V group on silicon, graphene-on-silicon, silicon-on-insulator, combinations thereof, and the like. Although described herein with respect to photodiodes 112, it is contemplated that any suitable light sensing component may be used. The photodiodes 112 may be configured to convert measured light into current. Photodiodes 112 may include the source and drain of an MOS transistor (not shown) that may transfer the current to other components, such as other MOS transistors. The other components may include a reset transistor, a current source follower or a row selector for transforming the current into digital signals, and the like. Although described as being dielectric, it is contemplated that the dielectric layer may include any suitable electrically insulating material.

CMOS image sensor layer 10 also includes metal wirings 105 formed in a dielectric layer 104. The metal wirings 115 may include interconnections for integrated circuit materials and external connections.

CMOS processing circuitry layer 20 is shown as a silicon substrate layer 101 for simplicity. However, it is understood that CMOS processing circuitry layer 20 can include CMOS circuits needed for the sequencing operation. For example, CMOS processing circuitry layer 20 can include circuitry for image process, signal processing, and control functions for sequencing operation, and external communication.

As shown in FIG. 1, CMOS image sensor layer 10 is configured for backside illumination (BSI). CMOS image sensor layer 10 and CMOS processing circuitry layer 20 can be fabricated separately and then joined together in a 3-D stacked device with a stacking layer 30. Stacking layer 30 can include a dielectric layer 102 and vias 103 formed in dielectric layer 102. Vias 103 are used for connecting CMOS image sensor layer 10 and CMOS processing circuitry layer 20.

FIG. 1 also shows a passivation layer 121 overlying CMOS image sensor layer 10. Passivation layer 121 may be deposited by conventional semiconductor processing techniques (e.g., low temperature plasma chemical vapor deposition, PECVD, sputtering, ALD, spin coating, dipping, etc.) on the substrate layer 110 and the photodiodes 112. The passivation layer 121 may include any suitable protective material. For example, the passivation layer 121 may include materials such as silicon nitride, silicon oxide, other dielectric material, or combinations thereof, and the like. The passivation layer 121 may act as an etch stop for later etching steps, as described further herein. The passivation layer 121 may alternatively or additionally act to protect the active device (i.e., the backside illumination CMOS sensor). The passivation layer 121 may alternatively or additionally act to protect photodiodes 112 from wear caused by frequent use. The passivation layer 121 may be transparent.

Discrete areas, sometimes called "spots" or wells (not shown), at which analyte molecules may be localized or immobilized may be formed over or in the first passivation layer 121. Chemical or biological samples may be placed on or over the discrete areas for analysis. In general, for DNA sequencing, the biological samples comprise a DNA sequencing library. DNBs or other members of a DNA sequencing library, or a clonal population thereof, are localized in the discrete areas.

In some embodiments, CMOS image sensor layer 10 may be adapted for detecting an optical signal (e.g., fluorescent or chemiluminescent emission) from a corresponding array of biomolecules, where individual biomolecules may be positioned over (e.g., in spots or wells) one or more photodiodes such that the one or more photodiodes receive light from the biomolecule. As used herein chemiluminescence includes bioluminescence, such as bioluminescence produced by luciferase reporters.

Figure 2:
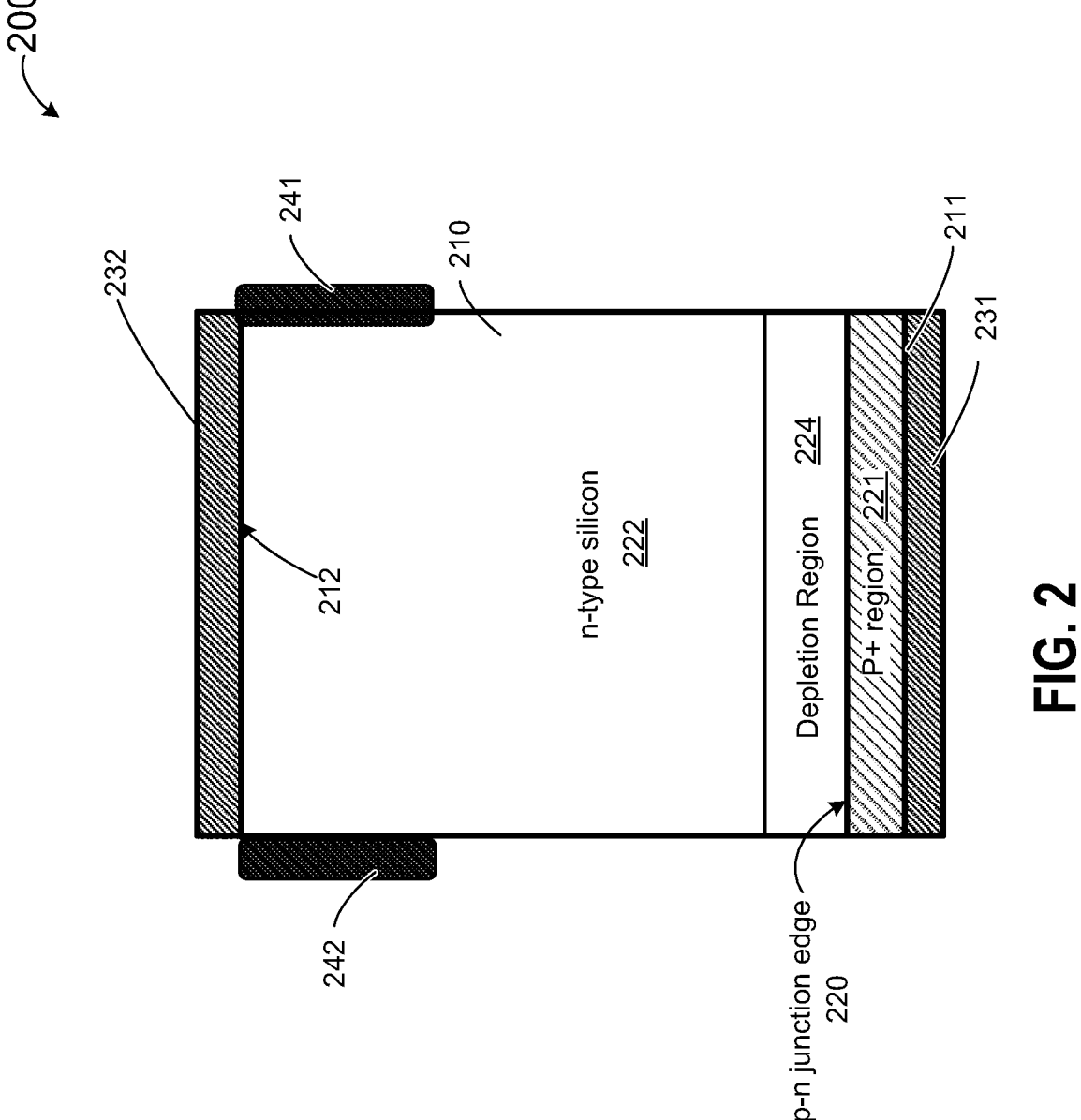
FIG. 2 is a cross-sectional view of a photodiode according to some embodiments of the invention.

FIG. 2 is a cross-sectional view of a photodiode according to some embodiments of the invention. Photodiode 200 is an example of photodiodes that can be used in backside illumination (BSI) CMOS image sensor described in FIG. 1. In this example, photodiode 200 is a silicon P-N junction photodiode. Photodiode 200 includes a semiconductor substrate 210 having a first surface 211 and a second surface 212. The second surface 212 is located opposite the first surface 211. Photodiode 200 includes and a light sensing junction 220 located adjacent to the first surface 211. In this example, light sensing junction 220 is a silicon P-N junction 220 formed by a heavily doped p+ region 221 in an n-type substrate region 222. A depletion region 224 is formed adjacent to the junction, where carriers can be generated by incoming photons and can be sensed as electrical signals. The first surface can also be referred to as the front surface, and the second surface can also be referred to as the back surface of the photodiode. Photodiode 200 can also have dielectric layers 231 and 232 covering the first surface 211 and the second surface 212, respectively.

In front side illumination (FSI) sensing, the incoming light is incident from the front surface, or the first surface, 211. In back side illumination (BSI) sensing, the incoming light is incident from the back surface, or the second surface, 212. In the example of FIG. 2, photodiode 200 is used for back side illumination (BSI), and the incoming light is incident upon the second surface 212. Photodiode 200 can also have deep trench isolation (DTI) regions 241 and 241 to isolate one photodiode from neighboring photodiodes. In some embodiments, trenches 241 and 242 can be filled with a metal, e.g., tungsten, W. A tungsten deep trench isolation (W DTI) can reduce the incident light from entering to neighboring photodiodes.

Figure 3:
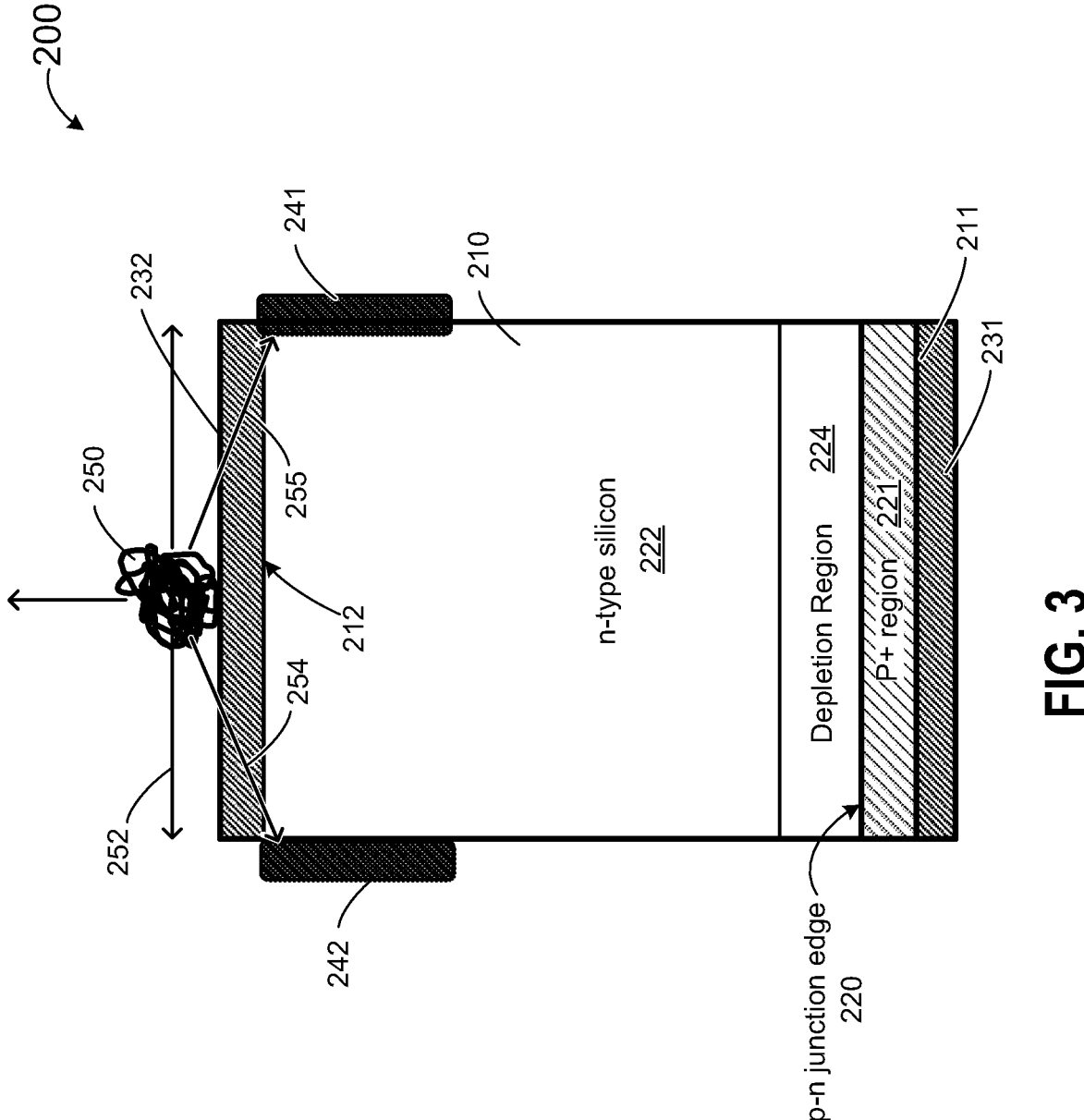
FIG. 3 is a cross-sectional view of the photodiode of FIG. 2, illustrating collection efficiency of light emitted by a biological sample according to some embodiments of the invention.

FIG. 3 is a cross-sectional view of the photodiode 200 of FIG. 2, illustrating collection efficiency of light emitted by a biological sample according to some embodiments of the invention. As shown in FIG. 3, a biological sample 250 is disposed on a backside of photodiode 200. An optical signal (e.g., fluorescent or chemiluminescent emission) in all directions from biological sample 250, as shown by light rays 252. However, only a portion of the emitted light can be collected by photodiode 200, as indicated by light rays 254 and 255. As a result, most of the emitted light is not collected and cannot contribute to the sensed signal.

Figure 4:
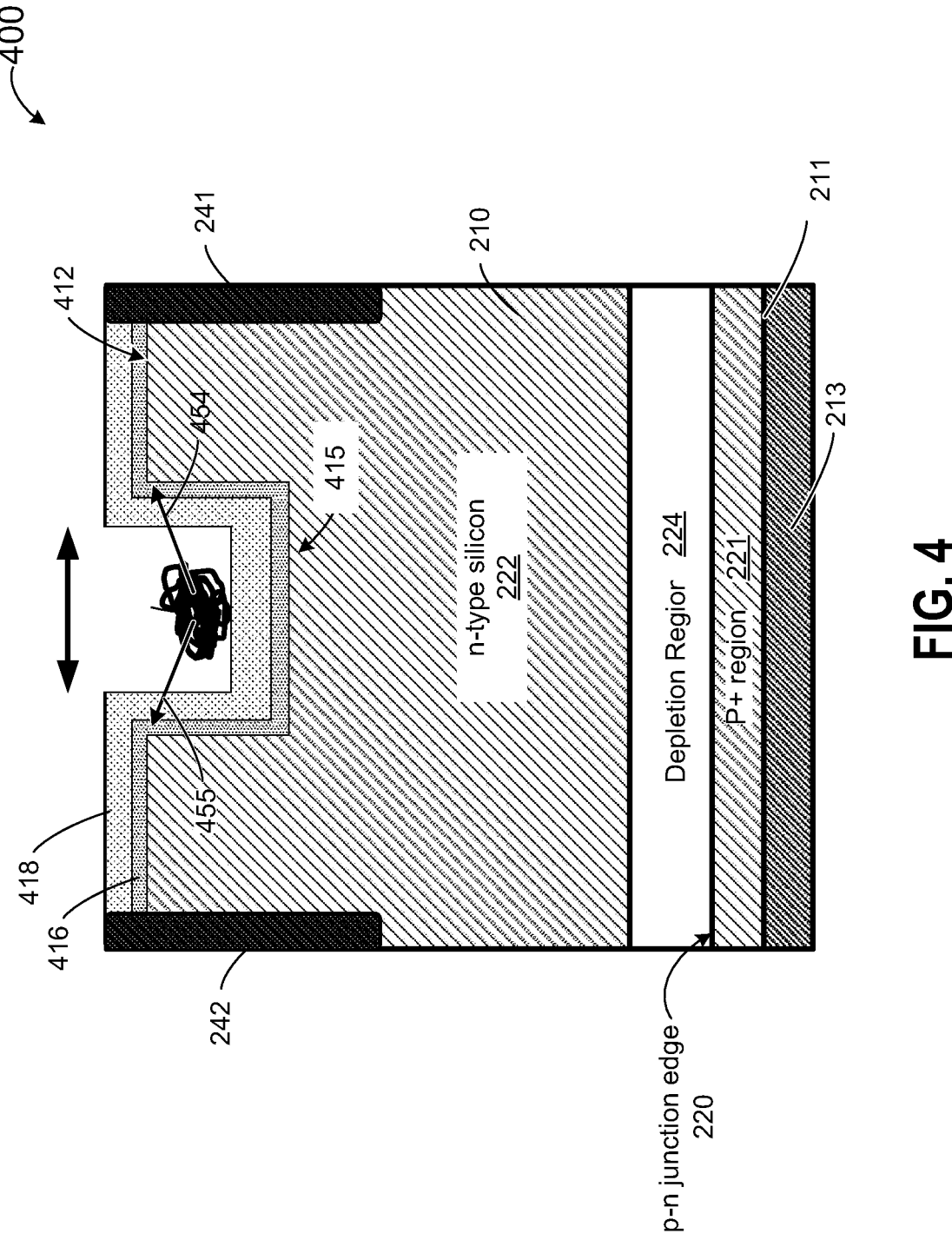
FIG. 4 is a cross-sectional view of a photodiode with improved light collection efficiency of light emitted by a biological sample according to some embodiments of the invention.

FIG. 4 is a cross-sectional view of a photodiode with improved light collection efficiency of light emitted by a biological sample according to some embodiments of the invention. As shown in FIG. 4, photodiode 400 is similar to photodiode 200 of FIG. 2, and similar components are shown using the same reference numerals. However, photodiode 400 has a second surface, or back surface, 412 that is different from the second surface 212 in FIG. 2. In FIG. 2, the second surface 212 has a substantially planar surface. However, the second surface 412 in FIG. 4 has a non-planar surface. The non-planar surface can be a concave surface covering a recessed region 415 in the semiconductor substrate. The recessed region is sized and functionalized to contain a biological sample 450, such as a nucleic acid macromolecule. As shown by light rays 454 and 455 in FIG. 4, most of the light emitted by biological sample 450 can be collected by photodiode 400. The light collection efficiency can be greatly improved.

The recessed region can be a trench etched in the silicon substrate. The recessed region 415 in FIG. 4 is substantially rectangular in shape. The second surface 412 is covered with a metal oxide layer 416. An oxide layer 418, such as a silicon oxide layer, is disposed over the metal oxide layer 416. In some embodiments, the metal oxide layer can be sandwiched thin layers of HfO2 and Ta2O5. The sandwiched thin layers of HfO2 and Ta2O5, can be used to depress dark current in the photodiode. In some embodiments, the photodiode 400 can include one or more dielectric layer overlying the second surface of the semiconductor substrate, a metal oxide layer overlying the one or more dielectric layers, and an silicon oxide layer overlying the metal oxide layer.

The recessed region in the semiconductor substrate can be formed using a dry etching process. For example, a dry etching process can include plasma etching, reactive ion etching (RIE), etc. A dry etching process can include different chemistries, for example, chlorine-based etching process or a fluorine-based dry etching process. Alternatively, the recessed region in the semiconductor substrate is formed using a wet etching process. For example, the wet etching process can be an isotropic etching process or a crystalline orientation dependent wet anisotropic etch. As an example of a crystalline orientation dependent wet anisotropic etch, the wet etching process comprises an etching process using KOH. Etching of silicon using aqueous KOH can creates V-shaped grooves, pyramid-shaped recessed area, etc.

Figure 5:
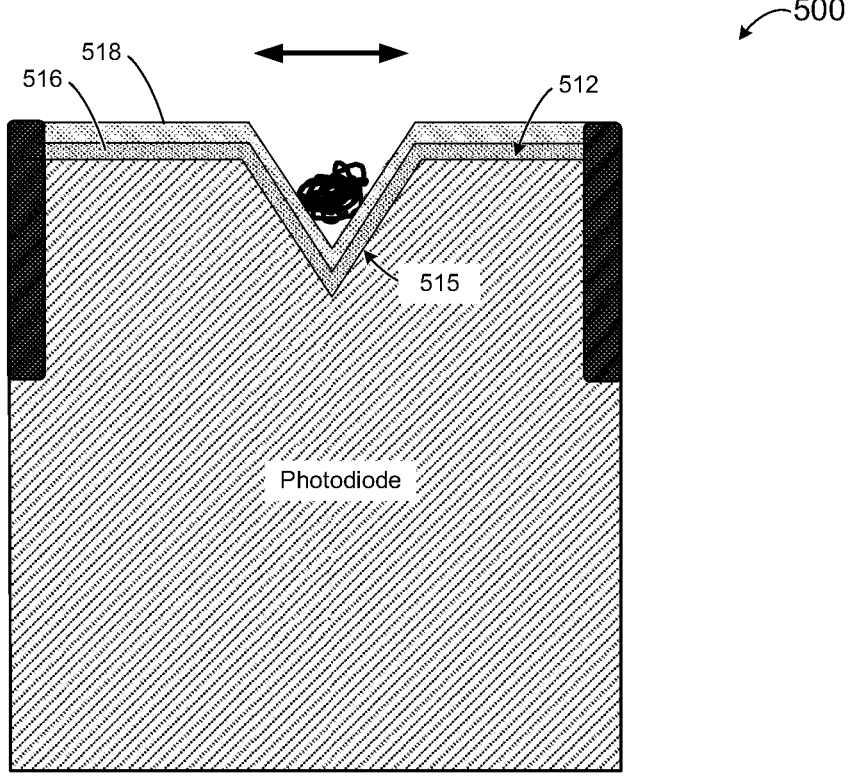
FIG. 5 is a cross-sectional view of a photodiode with improved light collection efficiency of light emitted by a biological sample according to alternative embodiments of the invention.

FIG. 5 is a cross-sectional view of a photodiode with improved light collection efficiency of light emitted by a biological sample according to alternative embodiments of the invention. As shown in FIG. 5, the recessed region 515 of pyramid shape is formed by a crystalline orientation dependent wet anisotropic etch using an etching process using KOH to etch silicon. Similar to photodiode 400 in FIG. 4, in photodiode 500 of FIG. 5, the second surface 512 is covered with a metal oxide layer 516. An oxide layer 518, such as a silicon oxide layer, is disposed over the metal oxide layer 516. In some embodiments, the metal oxide layer can be sandwiched thin layers of HfO2 and Ta2O5. The sandwiched thin layers of HfO2 and Ta2O5, can be used to depress dark current in the photodiode.

Figure 6:
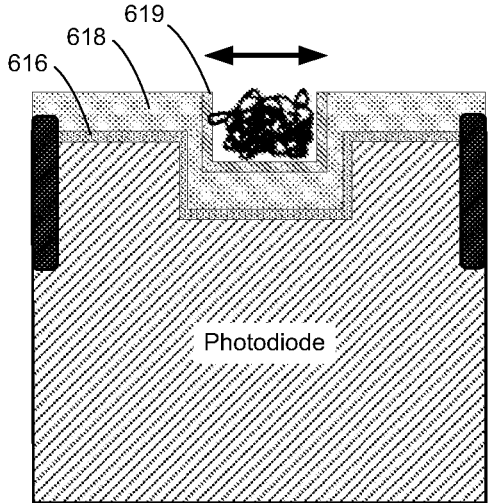
FIG. 6 is a cross-sectional view of another photodiode with improved light collection efficiency of light emitted by a biological sample according to some embodiments of the invention.
Figure 6:
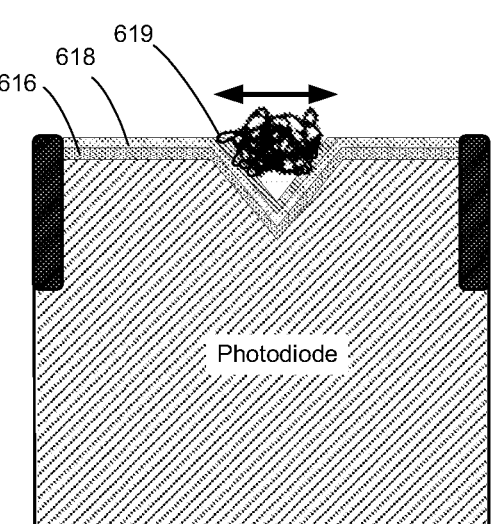

As described above, the recessed region is sized and functionalized to contain a nucleic acid macromolecule. For example, in photodiode 400 in FIG. 4, the surface of oxide layer 418 can be functionalized using chemicals on the oxide layer to immobilize DNBs. Alternatively, the surface of the oxide layer can be functionalized using an additional metal oxide layer formed on the oxide layer. As shown in FIG. 6, a metal oxide layer 619 is formed over the oxide layer 618. More details of functionalization of surface layer to retain biological samples are described in, for example, U.S. patent application Ser. No. 16/128,120, filed Sep. 11, 2018, entitled, "WAFER LEVEL SEQUENCING FLOW CELL FABRICATION," incorporated in its entirety by reference.

In some embodiments, the recessed region includes a trench with a substantially rectangular cross-section. In some embodiments, the recessed region can include a trench with a substantially square cross-section. The recessed region can be an etched region with a substantially pyramidal cross-section, a substantially circular cross-section, a substantially elliptical cross-section, a substantially pyramidal cross-section, a substantially circular cross-section, or a substantially elliptical cross-section.

In some embodiments, the recessed region includes a trench with a top opening having a substantially rectangular cross-section. In some embodiments, the recessed region can include a trench with a top opening having a substantially square cross-section. The recessed region can be an etched region with a top opening having a substantially pyramidal cross-section, a substantially circular cross-section, a substantially elliptical cross-section, a substantially pyramidal cross-section, a substantially circular cross-section, or a substantially elliptical cross-section.

In some embodiments, the trenches can have a width of from 200 nm to 300 nm, and a depth from 200 to 300 nm. In some embodiments, the trenches can have a width of from 100 nm to 500 nm, and a depth from 100 to 600 nm. In some embodiments, the trenches can have a width of from 20 nm to 500 nm, and a depth from 20 to 600 nm. In other embodiments, the trenches can have a width and a depth selected based on the size of the biological samples to improve the efficiency of light collection.

In some embodiments, the light sensing junction comprises a n+ region in a p-type substrate.

In some embodiments, the photodiode can include a metal-containing layer overlying the second surface of the semiconductor substrate, and a dielectric layer the metal-containing layer. The metal-containing layer can include a metal layer or a metal oxide layer. The dielectric layer can include silicon nitride, silicon oxide, other dielectric materials, or combinations thereof. In some embodiments, the photodiode can include a metal oxide layer overlying the second surface of the semiconductor substrate, and a silicon oxide layer overlying the metal oxide layer.

In some embodiments, the metal-containing layer (e.g., metal oxide layer) can have a thickness in the range of 50-150 nm. In other embodiments, the metal-containing layer layer can have a thickness in the range of 20-400 nm. The dielectric layer (e.g., oxide layer) can have a thickness in the range of 50-150 nm. In other embodiments, the metal oxide can have a thickness in the range of 20-400 nm.

The various thin film layers described above can be formed by conventional semiconductor thin film techniques, e.g., chemical vapor deposition (CVD), low temperature plasma chemical vapor deposition (LPCVD), plasma-enhanced chemical vapor deposition (PECVD), sputtering, physical vapor deposition (PVD), and atomic layer deposition (ALD), etc.

In some embodiments, the photodiode can include one or more dielectric layer overlying the second surface of the semiconductor substrate, a metal oxide layer overlying the one or more dielectric layers, and an silicon oxide layer overlying the metal oxide layer.

In some embodiments, the photodiode can include a metal oxide layer having one or more of hafnium oxide ($HfO2$) and tantalum oxide ($Ta2O5$). In some embodiments, the a metal oxide layer can be a sandwiched layers of hafnium oxide ($HfO2$) and tantalum oxide ($Ta2O5$).

In some embodiments, the metal oxide layer comprises one or more of anodized aluminum ($Al2O3$), tantalum oxide ($Ta2O5$), niobium oxide ($Nb2O5$), zirconium oxide ($ZrO2$), and titanium oxide ($TiO2$).

According to some embodiments, a biosensor can have a backside illumination complementary metal-oxide-semiconductor (CMOS) image sensor that includes an electronic circuit layer, and a photo sensing layer over the electronic circuit layer. The photo sensing layer includes a plurality of photodiodes overlying the electronic circuit layer. Each of the photodiodes has a light sensing junction adjacent to the electronic circuit layer and a light receiving surface opposite to the electronic circuit layer. The light receiving surface includes a concave surface covering a recessed region in a backside of the photodiode, and the recessed region is sized and functionalized to contain a nucleic acid macromolecule.

In some embodiments of the above biosensor, each of the photodiodes includes a photodiode as described herein. For example, FIG. 1 illustrates a plurality of backside illumination (BSI) CMOS biosensors. In FIG. 1, CMOS image sensor layer 10 includes a plurality of photodiodes 112. Each photodiode can have a structure similar to the photodiodes described above in connection with FIGS. 4-6, having a concave surface covering a recessed region in a backside of the photodiodes for receiving a sample that can improve light collection efficiency in biosensors for biological or chemical analysis.

In some embodiments, the electronic circuit layer includes a dielectric layer and a metal wiring formed in the first dielectric layer, wherein the metal wiring is configured to couple the plurality of photodiodes to an external device.

In some embodiments, the biosensor also includes a passivation layer over the backside illumination CMOS image sensor.

In some embodiments of the above biosensor, each photodiode of the plurality of photodiodes is configured to detect light emitted from a fluorescent or chemiluminescent label on a nucleic acid macromolecule of the plurality of nucleic acid macromolecules.

In some embodiments, the light is emitted from fluorescent labeled oligonucleotide probes hybridized to nucleic acid amplicons immobilized on the spots.

In some embodiments, the light is emitted from fluorescent labeled primer extension product hybridized to nucleic acid amplicons immobilized on the spots.

In some embodiments, the nucleic acid amplicons are from genomic DNA fragments or a cDNA library.

In some embodiments, the amplicons are formed by rolling circle amplification or bridge polymerase chain reaction (PCR).

In some embodiments, the biosensor also includes an excitation light source.

Some embodiments provide a method that includes providing a backside illumination complementary metal-oxide-semiconductor (CMOS) image sensor. Providing the backside illumination CMOS image sensor includes providing an electronic circuit layer and providing a photo sensing layer over the electronic circuit layer. The photo sensing layer includes an electronic circuit layer and a photo sensing layer over the electronic circuit layer. The photo sensing layer includes a plurality of photodiodes overlying the electronic circuit layer. Each of the photodiodes has a light sensing junction adjacent to the electronic circuit layer and a light receiving surface is defined by a surface of the plurality of photodiodes opposite to the electronic circuit layer. The light receiving surface includes a concave surface covering a recessed region in a backside of the photodiodes. The recessed region is sized and functionalized to contain a nucleic acid macromolecule.

In some embodiments of the above method, each of the photodiodes includes a photodiode as described herein.

In some embodiments, the light emitted from the nucleic acid macromolecule contained in the spot is received by the light receiving surface of one photodiode.

In some embodiments, the light emitted from the nucleic acid macromolecule contained in the spot is received from the light receiving surface of more than one photodiode.

In some embodiments, providing the electronic circuit layer includes depositing a dielectric layer and forming a metal wiring in the dielectric layer. The metal wiring is configured to couple the plurality of photodiodes to an external device.

In some embodiments, the method also includes depositing a passivation layer over the backside illumination CMOS image sensor.

In some embodiments, the method also includes attaching a nucleic acid macromolecule of the plurality of nucleic acid macromolecules to a spot of the plurality of spots.

In some embodiments, the method also includes detecting light emitted from a fluorescent or chemiluminescent label on the nucleic acid macromolecule using a photodiode of the plurality of photodiodes.

In some embodiments, the light is emitted from fluorescent labeled oligonucleotide probes hybridized to nucleic acid amplicons immobilized on the spots.

In some embodiments, the light is emitted from fluorescent labeled primer extension product hybridized to nucleic acid amplicons immobilized on the spots.

In some embodiments, the nucleic acid amplicons are from genomic DNA fragments or a cDNA library.

In some embodiments, the amplicons are formed by rolling circle amplification or bridge polymerase chain reaction (PCR).

In some embodiments, the method also includes illuminating the nucleic acid macromolecule with an excitation light source.

According to some embodiments, a method of nucleic acid sequencing includes iteratively performing a process that includes the following steps:

labeling a nucleic acid macromolecule with a fluorescent label that identifies a nucleotide base at a particular position in the nucleic acid macromolecule;

detecting the fluorescent label associated with the nucleic acid macromolecule, wherein detecting the fluorescent label includes:

illuminating the nucleic acid macromolecule with excitation light, wherein the nucleic acid macromolecule absorbs the excitation light and transmits emitted light onto a photodiode of a backside illumination (BSI) complementary metal-oxide-semiconductor (CMOS) image sensor;

measuring at least one parameter of the emitted light received at the photodiode; and correlating the at least one parameter of the emitted light to the fluorescent label; and removing the fluorescent label from the nucleic acid macromolecule.

In some embodiments of the above method, each of the photodiodes includes a photodiode as described herein.

According to some embodiments, a method of nucleic acid sequencing comprising iteratively performing a process that includes the following steps:

labeling a nucleic acid macromolecule with a chemiluminescent label that identifies a nucleotide base at a particular position in the nucleic acid macromolecule;

modifying the environment of the nucleic acid macromolecule chemiluminescent such that the label emits light;

wherein the emitted light is transmitted onto a photodiode of a backside illumination (BSI) complementary metal-oxide-semiconductor (CMOS) image sensor;

measuring at least one parameter of the emitted light received at the photodiode; and correlating the at least one parameter of the emitted light to the chemiluminescent label; and removing the chemiluminescent label from the nucleic acid macromolecule.

In some embodiments of the above method, each of the photodiodes includes a photodiode as described herein.

According to some embodiments, a biosensor has a backside illumination complementary metal-oxide-semiconductor (CMOS) image sensor that includes an electronic circuit layer and a photo sensing layer over the electronic circuit layer. The photo sensing layer includes a plurality of photodiodes overlying the electronic circuit layer. Each of the photodiodes has a light sensing junction adjacent to the electronic circuit layer and a light receiving surface is defined by a surface of the plurality of photodiodes opposite to the electronic circuit layer. The light receiving surface includes a concave surface covering a recessed region in a backside of the photodiodes. A protective layer above the light receiving surface that is sized and functionalized to contain a plurality of nucleic acid macromolecules.

In some embodiments of the above method, each of the photodiodes includes a photodiode as described herein.

The biological or chemical samples mentioned above may include any of a number of components. For example, a sample may contain nucleic acid macromolecules (e.g., templates, DNA, RNA, etc.), proteins, and the like. The sample may be analyzed to determine a gene sequence, DNA-DNA hybridization, single nucleotide polymorphisms, protein interactions, peptide interactions, antigen-antibody interactions, glucose monitoring, cholesterol monitoring, and the like.

As discussed above, in some embodiments the biomolecule is a nucleic acid, such as DNA. See U.S. Pat. Nos. 8,778,849; 8,445,194; 9,671,344; 7,910,354; 9,222,132; 6,210,891; 6,828,100; 6,833,246; 6,911,345, and Pat. App. Pub. No. 2016/0237488, herein incorporated by reference in their entireties. Without limitation, the DNA biomolecule may be a DNA nanoball (single stranded concatemer) hybridized to labeled probes (e.g., in DNB sequencing by ligation or cPAL methods) or to complementary growing strands (e.g., in DNB sequencing by synthesis methods) or both; or a single DNA molecule (e.g., in single molecule sequencing); or to a clonal population of DNA molecules, such as is created in bridge PCR-based sequencing. Thus, reference to "a biomolecule", "a DNA macromolecule" or "a nucleic acid macromolecule" may encompass more than one molecule (e.g., a DNB associated with multiple growing complementary strands or a DNA cluster comprising clonal population of hundreds or thousands of DNA molecules). Exemplary methods for making DNBs (e.g., DNB libraries) and for making arrays of discrete spaced apart regions separated by inter-regional areas are well known in the art. See, for example, U.S. Pat. Nos. 8,133,719; 8,445,196; 8,445,197; and 9,650,673, herein incorporated by reference in their entireties. In some embodiments DNBs or other macromolecules are immobilized on discrete spaced apart regions, or spots, through attractive noncovalent interactions (e.g., Van der Waal forces, hydrogen bonding, and ionic interactions). In some embodiments discrete spaced apart regions comprise functional moieties (e.g., amines). In some embodiments discrete spaced apart regions comprise capture oligonucleotides attached thereto, for binding template DNAs (e.g., DNBs). Generally the discrete spaced apart regions are arranged in a rectilinear pattern, however, regular arrays with other arrangements (e.g., concentric circles of regions, spiral patterns, hexagonal patterns, and the like) may be used.

In some embodiments, the nucleic acid macromolecules may be amplicons of genomic DNA fragments or a cDNA library. As used herein, an "amplicon" may be the product of amplification of a nucleic acid molecule, typically a fragment of genomic DNA or a cDNA library. Methods of amplification include, but are not limited to, rolling circle amplification, as described, for example, in U.S. Pat. No. 8,445,194 (herein incorporated by reference in its entirety), or bridge polymerase chain reaction (PCR), as described, for example, in U.S. Pat. No. 7,972,820, herein incorporated by reference in its entirety. The amplification may be performed before the nucleic acid is contacted with the biosensor, or in situ, as described, for example, in U.S. Pat. No. 7,910,354, herein incorporated by reference in its entirety.

For example, a biological sample, such as a DNA macromolecule, oligonucleotide, or nucleotide, associated with a fluorescent or chemiluminescent dye, may be placed above a photodiode. In the case of fluorescence, the dye may be illuminated by excitation light from an excitation light source. The excitation light may correspond to any suitable type or intensity of light, including, for example, visible light, infrared (IR), ultraviolet (UV), and the like. The excitation light may also come from any suitable source, such as light emitting diodes (LEDs), lamps, lasers, combinations thereof, and the like. When the dye is illuminated with excitation light at a certain wavelength, the biological sample may absorb the light, then emit light of a different wavelength. For example, the biological sample may absorb excitation light having a 450 nm wavelength, but emit light with a 550 nm wavelength. In other words, fluorescent light of a characteristic wavelength may be emitted when the dye is illuminated by light of a characteristic different wavelength (i.e., the excitation light source). Because excitation light is used to measure fluorescence, however, it must be filtered out in order to take accurate measurements at the photodiode 117.

In the case of chemiluminescence, no excitation light source is needed for the photodiodes to detect emitted light. Instead, the biological sample may emit light due to a chemical or enzymatic reaction that may occur between the biological sample and the chemiluminescent dye (or other solution), causing light to be emitted due to breaking or forming chemical bonds (e.g., the action of a luciferase protein on a luciferin substrate).

For both fluorescence and chemiluminescence, the photodiodes may detect the intensity of the emitted light and transform it into an electronic signal based on the intensity of the light that may be provided to an external device via metal wiring 105. The external device may correlate the electronic signal to a particular wavelength and brightness, based on the electronic signal.

In some embodiments, the active spot or well on the surface of the biosensor and the nucleic acid macromolecule may be mutually configured such that each spot binds only one nucleic acid macromolecule. This may be achieved, for example, by contacting the surface with amplicons that correspond in size to the active spot (e.g., an amplicon having a diameter that is effectively as large or larger than the diameter of the active spot). See U.S. Pat. No. 8,445,194, herein incorporated by reference in its entirety. Alternatively, the active spot can be chemically adapted to bind a single DNA fragment, which may then be amplified to fill a larger region at and around the original binding site.

Some embodiments of the invention may be used to determine different labels corresponding to different wavelengths of light. The labels may be, for example, fluorescent, chemiluminescent or bioluminescent labels. For example, in gene sequencing (or DNA sequencing), embodiments of the invention may be used to determine the precise order of nucleotide bases within a nucleic acid macromolecule (e.g., a strand of DNA). The nucleotide bases may be labeled with a specific fluorescent label (e.g., adenine (A), guanine (G), cytosine (C), or thymine (T)). Alternatively, one color, two color, or three color sequencing methods, for example, may be used.

With respect to fluorescence, each of the nucleotide bases may be determined in order by successively exciting the nucleic acid macromolecule with excitation light. The nucleic acid macromolecule may absorb the excitation light and transmit an emitted light of a different wavelength onto a biosensor as described herein. The biosensor may measure the wavelength of emitted light and intensity received by the photodiode. Each nucleotide (e.g., fluorescently labeled nucleotide), when excited by excitation light of a certain wavelength and/or intensity, may emit a certain wavelength of light and/or intensity into the photodiode, allowing identification of the presence of a particular nucleotide base at a particular position in the nucleic acid macromolecule. Once that particular nucleotide base has been determined, it may be removed from the nucleic acid macromolecule, such that the next successive nucleotide base may be determined according to a similar process.

A nucleic acid macromolecule may be labeled with one or more different fluorescent, chemiluminescent, or bioluminescent labels before or after attaching to the biosensor for any purpose. For example, the nucleic acid macromolecule may be hybridized with a labeled oligonucleotide probe or amplification primer. Alternatively, the nucleic acid macromolecule may be hybridized with a non-labeled oligonucleotide, which may then be ligated to a labeled probe, or extended using labeled nucleotide analogs. By way of illustration, the labeling may be done for the purpose of characterizing the nucleic acid macromolecule (for example, the presence of a single nucleotide polymorphism (SNP) associated with a disease), or for nucleic acid sequencing of all or a part of the nucleic acid macromolecule, as described above. DNA sequencing by probe hybridization is described, for example, in U.S. Pat. No. 8,105,771, herein incorporated by reference in its entirety. Sequencing by anchor probe ligation is described, for example, in U.S. Pat. No. 8,592,150, herein incorporated by reference in its entirety. Sequencing by synthesis is described, for example, in U.S. Pat. No. 7,883,869, herein incorporated by reference in its entirety. In general, sequencing by synthesis is a method in which nucleotides are added successively to a free 3' hydroxyl group provided by a sequencing primer hybridized to a template sequence, resulting in synthesis of a nucleic acid chain in the 5' to 3' direction. In one approach, another exemplary type of SBS, pyrosequencing techniques may be employed (Ronaghi et al., 1998, Science 281:363).

In some embodiments, the biosensor may be reversibly coupled to a flow cell (not shown). The nucleic acid macromolecule may be attached to the biosensor by contacting the biosensor with a liquid sample in the flow cell. The flow cell may include one or more flow channels that are in fluid communication with the reaction sites. In one example, the biosensor may be fluidicly and electrically coupled to a bioassay system. The bioassay system may deliver reagents to the reaction sites according to a predetermined protocol and perform imaging events. For example, the bioassay system may direct solutions to flow along the reaction sites. The solution may include four types of nucleotides having the same or different fluorescent labels. In some embodiments, the bioassay system may then illuminate the reaction sites using an excitation light source. The excitation light may have a predetermined wavelength or wavelengths. The excited fluorescent labels may provide emission signals that may be detected by the photodiodes.

A user may prepare for sequencing by contacting a biosensor according to described embodiments with nucleic acid amplicons, or with a nucleic acid that is subsequently amplified, such that the nucleic acid macromolecule binds and is retained by the active spots or wells, and excess nucleic acid macromolecule may be washed away. The nucleic acid macromolecules may be contacted beforehand or in situ with a labeled reagent. The biosensor may then be operated as described herein to determine light emitted on or around nucleic acid macromolecules on the array. The light may be quantified, or it may be sufficient to determine in a binary fashion which of the nucleic acid macromolecules on the surface have been labeled with labels that emit at a particular wavelength. Different probes or different nucleic acid analogs may be used concurrently that have labels that emit light at different wavelengths, for example, to determine different bases at a particular position in the sequence, or to sequence multiple locations.

Although described herein with respect to a backside illumination CMOS sensor, it is contemplated that embodiments of the invention may be similarly applied to a frontside illumination CMOS sensor. Further, it is contemplated that embodiments of the invention may similarly apply to any suitable biosensor, such as those biosensors described in U.S. Provisional Pat. App. No. 62/416,813, filed Nov. 3, 2016, which is herein incorporated by reference in its entirety.

Biosensors according to embodiments of the invention are not limited to a particular use. In one aspect, the biosensors of embodiments of the invention find particular use for massively parallel DNA sequencing. DNA sequencing technologies are well known (see, e.g., Drmanac et al., 2010, "Human genome sequencing using unchained base reads on self-assembling DNA nanoarrays," Science 327:78-81; Shendure & Ji, (2008, "Next-generation DNA sequencing," Nature Biotechnology 26:1135-45) and are therefore described only in general terms in sections below. The following paragraphs provide a brief initial discussion of sequencing and associated terminology so that certain features of the biosensors described below may be more easily understood.

A variety of DNA sequencing methods are known. In many approaches, large molecules (e.g., genomic DNA) are broken into many smaller fragments, each having a characteristic DNA sequence. In array based technologies, the fragments are distributed to an array of positions on a substrate so that each position in the array contains a DNA fragment with a single characteristic sequence. Sequence information ("reads") is obtained from DNAs at each of thousands, or more often, millions, of positions simultaneously and assembled by a computer. In most sequencing approaches, the fragments are amplified prior to sequence determination. The amplification may occur prior to the positioning of the fragments at each position, after the positioning of the fragments at each position, or both before and after positioning. The amplification step(s) produce "amplicons" which serve as "templates" in a sequencing process. Thus, for illustration, amplification may use RCA to produce a single-stranded concatemer (e.g., a DNA nanoball) at each position on the array or use bridge PCR to produce a clonal population (or cluster) of DNA molecules with the same sequence at each position.

It will be understood that reference to a "DNA macromolecule," and the like, encompasses DNA nanoballs, branched structures, and clustered clonal populations (i.e., more than a single molecule) or their precursors. In addition, a "DNA macromolecule," and the like, may encompass auxiliary DNA molecules such as primers and growing strands produced by primer extension or other processes encompasses. In many sequencing technologies, it is the auxiliary DNA molecules that comprise (or are "labeled" with) a detectable (e.g., fluorescent or chemiluminescent) dye that emit light detected by photodiodes of the biosensor. Thus, a phrase such as "illuminating the nucleic acid macromolecule with an excitation light source and detecting light emitted from the macromolecule" will be understood to encompass "exposing a DNA nanoball or clonal cluster and associated labeled auxiliary molecules with an excitation light source and detecting light emitted from the dyes of the labeled auxiliary molecules."

In array-based sequencing methods, and the biosensors of embodiments of the invention, DNA macromolecules are positioned on a substrate in wells or on "spots." The wells or spots are able to receive and retain the macromolecule. Often, the spots, sometimes called "discrete spaced apart regions" or "pads", comprise a substrate functionalized to receive a nucleic acid macromolecule and the spots are separated by areas that are "inert" in the sense that DNA macromolecules do not bind such areas. For example, and without limitation, see Drmanac 2010, supra. "Wells" are a type of spot comprising walls that form a boundary or barrier to the DNA macromolecules. Except where clear from context, reference to "spots" below may include wells.

In biosensors of embodiments of the invention, spots generally have uniform dimensions and are organized as a regular (i.e., not random) array. The spots of an array are generally organized in a rectilinear pattern, often in columns and rows, but other regular patterns may be used (e.g., a spiral). The spots of an array may have characteristic dimensions, pitch, and density. The spots themselves may be circular, square, hexagonal or other shape. In the discussion below, the spots are generally assumed to be circular (i.e., can be described as having a diameter). It will be understood that reference to a "diameter" can also refer to linear dimensions of other shaped spots (e.g., diagonal, length or width). Thus, as used herein, "linear dimension" can refer to a diameter of a circle, width of a square, diagonal, and the like. In the context of biosensors of embodiments of the invention, the size of the spots is meaningful in two ways. First, the spots may be sized and/or functionalized in a way that limits occupancy to a single target sequence. This may be a single DNA nanoball (a concatemer of a single target sequence) or a clonal cluster with a single target sequence. See, e.g., U.S. Pat. No. 8,133,719 and U.S. Pat. App. Pub. No. 2013/0116153, both incorporated by reference in their entireties for all purposes. Secondly, generally the spots may be sized and positioned relative to underlying photodiodes so that each photodiode receives emitted light from a single spot. In some embodiments, an array of spots may be positioned over an array of corresponding photodiode(s)

(and/or color filters) with a 1 to 1 correlation. That is, light emitted from an, e.g., DNA macromolecule at individual spot passes into an underlying filter and light not blocked by the filter is detected by a single photodiode associated with the filter, or light emitted from an, e.g., DNA macromolecule, at individual spot passes into a plurality of underlying filters, each associated with a filter (specific for particular wavelengths), each associated with a single photodiode, and light not blocked by a filter is detected by the associated photodiode. Thus, as also discussed below, in some embodiments, light emitted from a single spot may be detected by more than one photodiode (e.g., 2, 3, 4, etc.) photodiodes. In these embodiments, a group of multiple photodiodes associated with a single spot may be referred to as a "unit cell" of photodiodes. The spots and filters (e.g., single filters or unit cells) may be arranged in the biosensor such that each photodiode in the unit cell receives light emitted from the same single spot. In addition, in some embodiments, the area of the light receiving surface of a photodiode, or combined area of the light receiving surfaces of multiple photodiodes associated with the same spot, is less than the area of the spot (from which light is emitted). Put another way, the spot may be smaller than the underlying photodiode(s) such that the boundary of the spot, if projected onto the light receiving surface of the photodiode(s), is contained within the light receiving surface.

As is well known, nucleic acid sequencing generally involves an iterative process in which a fluorescent or chemiluminescent label is associated in a sequence in a specific way with the DNA template (amplicon) being sequenced, the association is detected, and the label is removed in the sense that it no longer emits a signal. See, e.g., U.S. Pat. App. Pub. No. 2016/0237488; U.S. Pat. App. Pub. No. 2012/0224050; U.S. Pat. Nos. 8,133,719; 7,910, 354; 9,222,132; 6,210,891; 6,828,100, 6,833,246; and 6,911, 345, herein incorporated by reference in their entireties. Thus it will be appreciated that, for example, "labeling a nucleic acid macromolecule with a fluorescent label" may refer to associating a labeled auxiliary molecule(s) with a DNA template immobilized on a spot.

As described above, biological or chemical samples may be placed on each of the described in biosensors above the photodiodes. The biological or chemical sample may include any of a number of components. For example, the sample may contain nucleic acid macromolecules (e.g., DNA, RNA, etc.), proteins, and the like. The sample may be analyzed to determine a gene sequence, DNA-DNA hybridization, single nucleotide polymorphisms, protein interactions, peptide interactions, antigen-antibody interactions, glucose monitoring, cholesterol monitoring, and the like.

As discussed above, in some embodiments the biomolecule is a nucleic acid, such as DNA. Without limitation, the DNA biomolecule may be a DNA nanoball (single stranded concatemer) hybridized to labeled probes (e.g., in DNB sequencing by ligation or cPAL methods) or to complementary growing strands (e.g., in DNB sequencing by synthesis methods) or both; or to a single DNA molecule (e.g., in single molecule sequencing); or to a clonal population of DNA molecules, such as is created in bridge PCR based sequencing. Thus, reference to "a biomolecule", "a DNA macromolecule" or "a nucleic acid macromolecule" may encompass more than one molecule (e.g., a DNB associated with multiple growing complementary strands or a DNA cluster comprising clonal population of hundreds or thousands of DNA molecules). See, e.g., U.S. Pat. No. 8,133, 719; U.S. Pat. App. Pub. No. 2013/0116153, U.S. Pat. App. Pub. No. 2016/0237488; U.S. Pat. App. Pub. No. 2012/

0224050; U.S. Pat. Nos. 8,133,719; 7,910,354; 9,222,132; 6,210,891; 6,828,100, 6,833,246; and 6,911,345, herein incorporated by reference in their entireties.

To achieve high density and assist in alignment between the nucleic acid macromolecules and the photodiodes of the biosensor, the surface of the biosensor may be constructed such that there are active spots or wells (e.g., the recessed regions in FIGS. 3-5) that are sized and chemically functionalized to receive a nucleic acid macromolecule, surrounded by areas of the surface to which the nucleic acid macromolecules may not bind. The nucleic acid macromolecules may be secured to the active surface aligned with the photodiode using any suitable surface chemistry. This may include non-covalent interaction (for example, to an area bearing positive charge) or interaction with a capture probe or oligonucleotide attached to the surface, bearing a sequence that is complementary to a sequence contained in the nucleic acid macromolecule. See, for example, U.S. Pat. No. 8,445,194, which is herein incorporated by reference in its entirety.

The biological or chemical samples may include any of a number of components. For example, a sample may contain nucleic acid macromolecules (e.g., DNA, RNA, etc.), proteins, and the like. The sample may be analyzed to determine a gene sequence, DNA-DNA hybridization, single nucleotide polymorphisms, protein interactions, peptide interactions, antigen-antibody interactions, glucose monitoring, cholesterol monitoring, and the like.

Although the processes described herein are described with respect to a certain number of steps being performed in a certain order, it is contemplated that additional steps may be included that are not explicitly shown and/or described. Further, it is contemplated that fewer steps than those shown and described may be included without departing from the scope of the described embodiments (i.e., one or some of the described steps may be optional). In addition, it is contemplated that the steps described herein may be performed in a different order than that described.

In the foregoing description, aspects of the application are described with reference to specific embodiments thereof, but those skilled in the art will recognize that the invention is not limited thereto. Thus, while illustrative embodiments of the application have been described in detail herein, it is to be understood that the inventive concepts may be otherwise variously embodied and employed, and that the appended claims are intended to be construed to include such variations, except as limited by the prior art. Various features and aspects of the above-described invention may be used individually or jointly. Further, embodiments can be utilized in any number of environments and applications beyond those described herein without departing from the broader spirit and scope of the specification. The specification and drawings are, accordingly, to be regarded as illustrative rather than restrictive. For the purposes of illustration, methods were described in a particular order. It should be appreciated that in alternate embodiments, the methods may be performed in a different order than that described.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the disclosure to the specific form or forms disclosed, but on the contrary, the intention is to cover all modifications, alternative constructions and equivalents falling within the spirit and scope of the disclosure, as defined in the appended claims.

What is claimed is:

1. A biosensor, comprising:
a backside illumination complementary metal-oxide-semiconductor (CMOS) image sensor including:
an electronic circuit layer; and
a photo sensing layer over the electronic circuit layer, wherein the photo sensing layer includes a plurality of photodiodes overlying the electronic circuit layer, and wherein each of the photodiodes has a light sensing junction adjacent to the electronic circuit layer and a light receiving surface opposite to the electronic circuit layer;
wherein the light receiving surface includes a concave surface covering a recessed region in a backside of the photodiode, and the recessed region is sized and functionalized to contain a nucleic acid macromolecule;
wherein the light receiving surface comprises one or more dielectric layers, a metal oxide layer overlying the one or more dielectric layers, and a silicon oxide layer overlying the metal oxide layer.

2. The biosensor of claim 1, wherein the light sensing junction comprises a P-N junction.

3. The biosensor of claim 1, wherein the metal oxide layer comprises sandwiched layers of tantalum pentoxide (Ta2O5) and hafnium oxide (HfO2), and the oxide layer comprises silicon oxide.

4. The biosensor of claim 1, wherein the metal oxide layer comprises $HfO_2$, $Al_2O_3$, $Ta_2O_5$, $Nb_2O_5$, $ZrO_2$, $TiO_2$, or a combination thereof.

5. The biosensor of claim 1, wherein the recessed region is formed using a wet etching process.

6. The biosensor of claim 5, wherein the wet etching process comprises a crystalline orientation dependent wet anisotropic etch.

7. The biosensor of claim 1, wherein the recessed region comprises a trench with a substantially rectangular, V-shaped, square, pyramidal, circular, or elliptical cross-section.

8. The biosensor of claim 1, wherein the recessed region comprises a trench with a top opening having a substantially rectangular, square, pyramidal, circular, or elliptical cross-section.

9. The biosensor of claim 1, wherein the electronic circuit layer comprises:
a dielectric layer; and
a metal wiring formed in the dielectric layer, wherein the metal wiring is configured to couple the plurality of photodiodes to an external device.

10. The biosensor of claim 1, further comprising:
a passivation layer over the backside illumination CMOS image sensor.

11. The biosensor of claim 1, wherein each photodiode of the plurality of photodiodes is configured to detect light emitted from a fluorescent or chemiluminescent label on a nucleic acid macromolecule.

12. A method of using the biosensor of claim 1, wherein the method comprises using the biosensor such that the light emitted from the nucleic acid macromolecule contained on the concave surface covering the recessed region is received by the light receiving surface of one photodiode.

13. The method of claim 12, further comprising:
attaching a nucleic acid macromolecule to a concave surface covering a recessed region.

14. The method of claim 13, further comprising:
detecting light emitted from a fluorescent or chemiluminescent label on the nucleic acid macromolecule using a photodiode of the plurality of photodiodes.

* * * * *